United States Patent [19]

Fujimoto et al.

[11] Patent Number: 4,520,201

[45] Date of Patent: May 28, 1985

[54] SYNTHESIS OF CIMETIDINE AND ANALOGS THEREOF

[75] Inventors: Michitaro Fujimoto, Tondabayashi; Hironori Ohde, Habikino; Hirokazu Seki, Nara; Shuhei Takamatsu, Sakai; Takeshi Sakai, Nara, all of Japan

[73] Assignee: Fujimoto Pharmaceutical Corp., Japan

[21] Appl. No.: 508,182

[22] Filed: Jun. 27, 1983

[30] Foreign Application Priority Data

Aug. 19, 1982 [JP] Japan .................................. 57-143568

[51] Int. Cl.³ .......................................... C07D 233/64
[52] U.S. Cl. ..................................... 548/342; 548/198
[58] Field of Search ........................................ 548/342

[56] References Cited

PUBLICATIONS

March, J., *Advanced Organic Chemistry*, McGraw Hill, New York, 1968, pp. 519–520.

*Primary Examiner*—Richard A. Schwartz
*Attorney, Agent, or Firm*—Omri M. Behr

[57] ABSTRACT

There is provided a process for producing cyanoguanidine derivatives, especially N-cyano-N'-Methyl-N''-(4-methyl-5-imidazolylmethyl)thioethyl-guanidine.

10 Claims, 2 Drawing Figures

SYNTHESIS OF CIMETIDINE AND ANALOGS THEREOF

BACKGROUND OF THE INVENTION

A variety of processes are known for synthesizing cimetidine (VI)

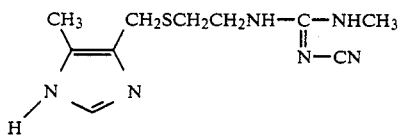

a compound known to have $H_2$-receptor antagonist activity and be of value as a drug for the treatment of gastric and duodenal ulcers.

These processes are disclosed in Japanese Published and Unexamined Patent Applications Kokai Nos. 50-32174, 51-54561, 51-125074 and 54-59275 and Japanese Patent Publication No. 56-1309. These processes, however, are not free from commercial problems; some of them require chromatographic purification of the reaction product and others require use of cysteamine which is an expensive reagent. There also is known a process in which the sodium salt of 4-methyl-5-mercaptomethylimidazole is reacted with N-cyano-N'-methyl-N''-(2-bromethyl)guanidine (Japanese Published and Unexamined Patent Application No. 54-130566) but since the starting material imidazole compound tends to be oxidized under alkaline conditions, the yield of the product is inevitably low. The purpose of the present invention is to overcome these disadvantages.

SUMMARY OF THE INVENTION

Completely unlike the conventional reactions of cimetidine synthesis, the process of this invention is characterized in that the comtemplated compound cimetidine (VI) and its analogs is produced by N-cyano-N'-alkyl-N''-(2-mercaptoethyl)-N'-[(4-methyl-5-imidazolylmethyl)] guanidine of the formula [V]:

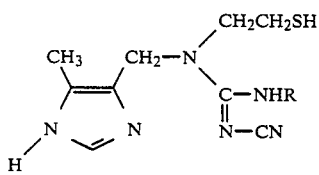

wherein R is lower alkyl, of 1-5 carbon atoms.

To produce the guanidine V a 4-methyl-5-halomethylimidazole of formula (I) or halogen acid salt thereof:

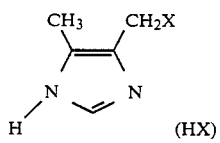

wherein X is chloro, bromo or iodo is first reacted with N-cyano-N',S-ethyleneisothiourea of the formula (II):

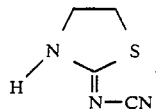

under basic conditions to give N-cyano-N',S-ethylene-N'-[(4-methyl-5-imidazolyl)methyl]isothiourea of the formula (III):

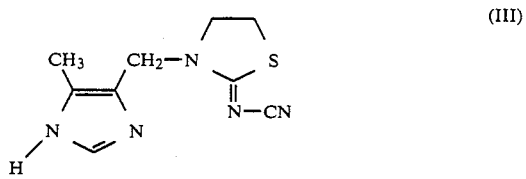

Then, this isothiourea derivative is reacted with an alkylamine IV, whereupon the thiazolidine ring undergoes fission to yield the starting guanidine which is then converted into the alkali metal salt.

$$R-NH_2 \quad (IV)$$

wherein R is defined above.

DESCRIPTION OF THE PREFERRED EMBODIMENTS

A 4-methyl-5-halo imidazole I or its and addition salt, suitably the 5-chloro, 5-bromo or 5-iodo compound or its hydrohalide or hydrosulfate salt is condensed with N-cyano-N',S-ethylene isothiourea.

In the practice of this invention, a basic substance is used as a condensing agent. The basic substance is exemplified by hydroxides carbonates, alkoxides of 1-5 carbon atoms or hydrides, of alkali metals such as sodium potassium, suitably sodium hydroxide, potassium hydroxide, sodium carbonate, potassium carbonate, sodium alkoxide, potassium alkoxide, sodium hydride, potassium hydride, etc. Alkali metals themselves such as metallic sodium, metallic potassium, metallic lithium, etc. may also be used.

The reaction is suitably carried out in a solvent. This solvent may be an alcohol e.g. preferably a lower alkanol such as methanol, ethanol, etc., a dialkyl ketone such as acetone, an ether suitably a dialkyl ether such as ethyl ether, or a non-hydroxylic solvent such as dimethylformamide, dimethyl sulfoxide or the like.

The reaction may be conducted in a broad temperature range from room temperature to the reflux temperature of the solvent and generally goes to completion in 2 to 3 hours.

The excess of compound II after the reaction is recovered in the isolation stage of product compound III and may be reused.

The ring fission reaction is carried out using any desired alkylamine, where cimetidine is the desired product methylamine employed. The reaction may be solvated by the reagent alkylamine itself or by a solvent.

Suitably examples of the solvent to be used in carrying out the reaction according to the invention are alcohols suitably alkanols such as methanol or ethanol, alkyl ketones such as acetone, and other polar solvents such as acetonitrile, dimethylformamide and dimethyl sulfoxide. However, the use of undiluted methylamine allows the reaction to proceed more efficiently.

The above reaction is complete in 1–2 hours at room temperature. Removal of the solvent by distillation following the reaction directly gives the desired compound V.

The guanidine V is converted into its alkali metal salt which in turn is converted by heat into the cyanoguanidine VI.

In the preferred procedure the guanidine V is treated with an alkali metal alkoxide or alkali metal hydride in a reaction inert solvent to yield the alkali metal salt which preferably, but not critically is not isolated but heated in situ to yield the desired cyanoguanidine. The alkali metal may, for example, be potassium, sodium or lithium.

The reaction solvent for the rearrangement of guanidine V to cyanoguanidine VI is preferably a polar solvent such as diethylene glycol, tertiary butanol or dimethylformamide.

The reaction temperature may range broadly from 40° C. to 150° C. The reaction time may be as short as 1 to 3 hours.

The process is not limited to the preferred embodiment. The solvent may be removed from the alkali metal salt of V which is subsequently heated with or without the presence of solvent under similar temperature conditions to yield the same cyanoguanidine IV.

The process according to this invention does not require expensive reactants nor does it require a complicated reaction procedure. For the isolation of the product compound, the process does not require a time-consuming procedure such as chromatography, either.

EXPERIMENTAL

EXAMPLE 1

Figure 1:
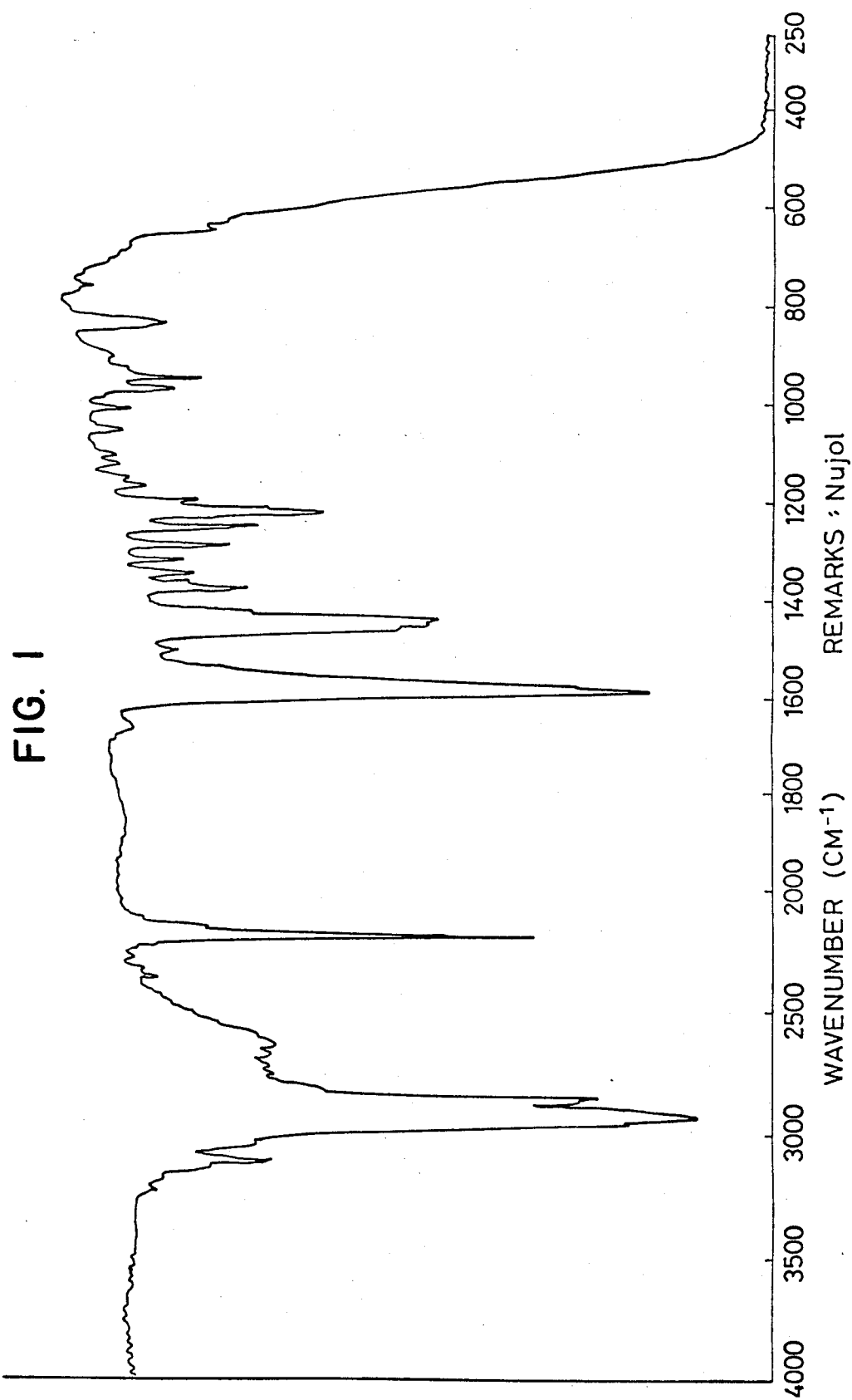
FIG. 1 is an IR spectrum (Nujol) of Compound III prepared in Example 1.
Figure 2:
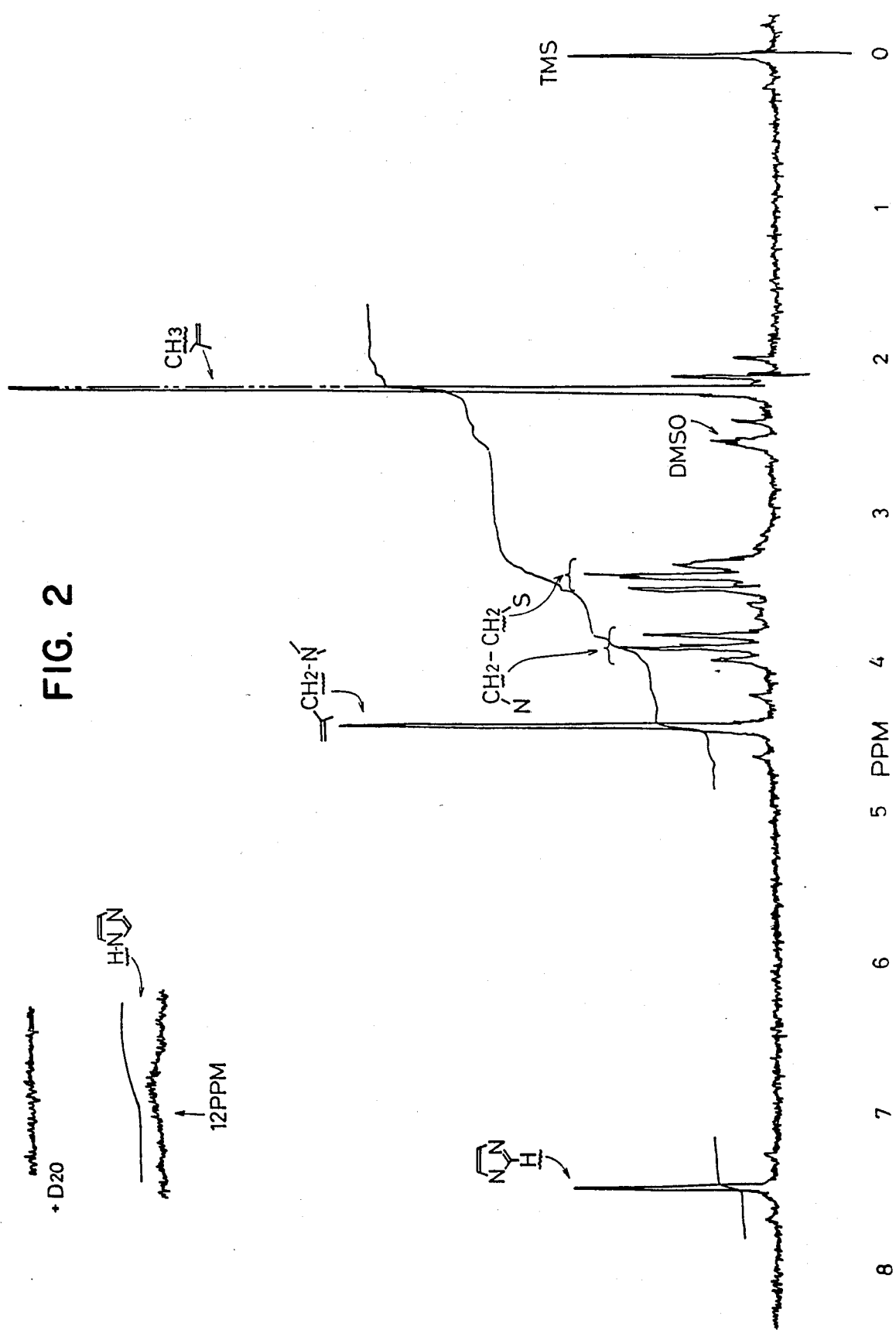
FIG. 2 is an NMR spectrum (DMSO) of Compound III prepared in Example 1.

To 20 ml of dimethylformamide was added 0.288 g of 50% sodium hydride, followed by gradual addition of 0.76 g (6.0×10$^{-3}$ moles) of N-cyano-N'S-ethyleneiothiourea (II). The mixture was stirred for 10 minutes, after which 0.5 g (3.0×10$^{-3}$ moles) of 4-methyl-5-chloromethylimidazole hydrochloride (I) was added gradually over a period of 30 minutes. The reaction mixture was stirred for 3 hours, at the end of which time the solvent was removed by evaporation. The residue was made acidic with 1 N-HCl, whereupon the excess N-cyano-N'-S-ethyleneisothiourea separated out as a precipitate and was recovered by filtration. The filtrate was made alkaline with potassium carbonate and the resultant crystals were collected by filtration and recrystallized from ethanol to give N-cyano-N',S-ethylene-N'[(4-methyl-5-imidazolyl)methyl] isothiourea (III) 0.51 g (79.6%).

m.p. 183°–184° C.

$C_9H_{11}N_5S$ requires (%): C, 48.85; H, 5.01; N, 31.65 found (%): C, 48.61; H, 5.02; N, 31.62; ir (Nujol): 2200, 1590 cm$^{-1}$ nmr (DMSO-d$_6$): δ 2.20 (S,—C<u>H</u>$_3$, 3H), δ 3.20~3.60 (t, NCH$_2$C<u>H</u>$_2$S, 2H), δ 3.76~4.10 Ct, NCH$_2$ CH$_2$S,2H), δ 4.43 (S,

2H) δ 7.46 (S,

1H), δ11.5~12.1 (b,

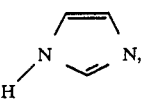

1H)

In accordance with the above procedure but starting with 4-methyl-5-bromo, or 5-iodo methylimidazole hydrohalide in place of the 5-chloro compound, the same product was obtained.

Further similarly but starting with the free imidazole in place of its acid addition salt the same product is obtained.

EXAMPLE II

To 20 ml of methylamine was added 370 mg (1.67×10$^{-3}$ moles) of N-cyano-N',S-ethylene-N'-[(4-methyl-5-imidazolyl)-methyl]isothiourea (III) and the mixture stirred at room temperature for 1 hour. The methylamine was then distilled off to give N-cyano-N'-methyl-N''-(2-mercaptoethyl)-N'''-[(4-methyl-5-imidazolyl)methyl]guanidine (V).

For identifying the compound (V) thus obtained, the following treatment was carried out.

The above sample of III was dissolved in a solution composed of 60 mg of sodium hydroxide, 0.5 ml of water and 5 ml of ethanol. A solution of 339 mg of 2,4-dinitrochlorobenzene in 5 ml of ethanol was separately prepared and added to the above ethanol solution, and the mixture was refluxed for 10 minutes and it was quickly filtered, and the filtrate was cooled. Crystals appeared upon triturating the vessel wall. The crystals were collected by filtration and recrystallized from ethanol to give the dinitrochlorobenzene derivative of compound (III). Yield 0.49 g, melting point 206°–207° C.

$C_{16}H_{18}N_8O_4S$ requires (%): C, 45.93; H 4.34; N,26.78. found (%): C,45.61; H,4.29; N,26.75 ir (Nujol): 2175, 1620, 1590, 1345; nmr (DMSO-d$_6$): δ 2.20 (S,

3H) δ2.90~3.16 (d.-NH—CH$_3$, 3H), δ 3.20~3.75 (m, NCH$_2$ CH$_2$S, 4H), δ 4.36 (S,

2H), 7.55 (S,

1H), δ 7.93~8.99 (m,

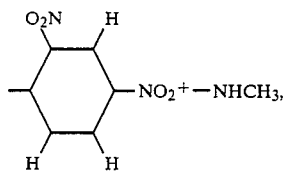

4H), δ 11.76~12.10 (broad,

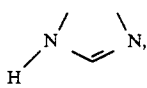

1H)

In accordance with the above procedure but where in place of methylamine there is used ethylamine, or propylamine there is obtained the corresponding N-ethyl, N-propyl compound.

EXAMPLE III (Synthesis of cimetidine VI)

In a nitrogen stream, 252 mg ($1.0 \times 10^{-3}$ moles) of N-cyano-N'-methyl-N''-mercaptoethyl-N'''-[(4-methyl-5-imidazolyl)methyl]guanidine (V) and 48 mg of 50% NaH (in mineral oil) was added to 10 ml of dimethylformamide and the mixture stirred at 80° C. After 3 hours of stirring, the solvent was evaporated and 5 N-sodium hydroxide (2 ml) was added. The mixture was extracted twice with ethyl acetate (4 ml). The ethyl acetate layer was reextracted into 1 N-HCl, the aqueous layer made alkaline with 5 N-NaOH and are extracted twice with ethyl acetate (4 ml). The ethyl acetate layer was decolorized with activated carbon and dried over anhydrous sodium sulfate and filtered. The solvent was then distilled off from the filtrate and the residue crystallized from a solvent mixture of ether, acetonitrile and petroleum ether to give cimetidine (VI). The melting point 139~141° C. and infrared absorption spectrum of ths product were in agreement with those of an authentic sample of cimetidine. Yield 0.21 g (82%).

In accordance with the above procedure but where in place of sodium hydride there is used sodium methylante, the same product is obtained.

In accordance with the above procedure, but where in place of N-cyano-N'-methyl-N''-mercaptoethyl-N'-[(4-methyl-5-imidazoyl)methyl] guanidine, the corresponding N'-methyl, N-propyl analog is used there is obtained the corresponding N'-ethyl, or N'-propyl analogs of the principal product were obtained.

We claim:

1. A process for producing a cyanoguanidine derivative of the formula:

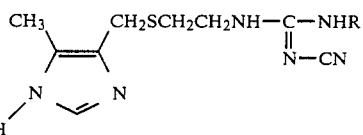

wherein R is lower alkyl of 1-5 carbon atoms which comprises heating an alkali metal salt of a compound of the formula:

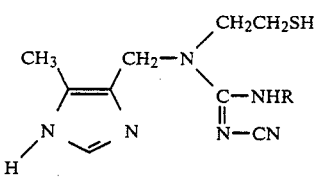

at between 40° and 100° C.

2. A process of claim 1 wherein the heating is carried out in a polar organic solvent.

3. A process of claim 2 wherein the solvent is diethyleneglycol, tert butanol or dimethyl formamide.

4. A process of claim 1 wherein the alkali metal is potassium, sodium or lithium.

5. A process of claim 4 wherein R is methyl.

6. A process for producing a cyanoguanidine derivative of the formula:

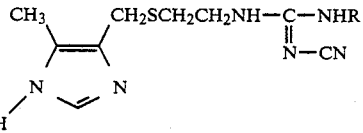

wherein R is lower alkyl of 1-5 carbon atoms which comprises reacting a compound of the formula:

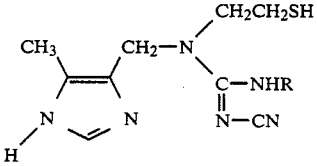

at between 40° and 100° C. with alkali metal alkoxide or alkali metal hydride in a reaction inert solvent.

7. A process of claim 1 wherein the reaction insert solvent is a polar organic solvent.

8. A process of claim 2 wherein the solvent is diethyleneglycol, tert butanol or dimethyl formamide.

9. A process of claim 1 wherein the alkali metal is potassium, sodium or lithium.

10. A process of claim 4 wherein R is methyl.

* * * * *